(12) United States Patent
Moon et al.

(10) Patent No.: US 8,764,770 B2
(45) Date of Patent: Jul. 1, 2014

(54) SUTURING DEVICE FOR ORGAN

(75) Inventors: Kyeong Tag Moon, Seoul (KR); Yoon Ha Shin, Seoul (KR); Young Gyu Lim, Seoul (KR)

(73) Assignee: Samji Electronics, Seoul (KR)

( * ) Notice: Subject to any disclaimer, the term of this patent is extended or adjusted under 35 U.S.C. 154(b) by 281 days.

(21) Appl. No.: 13/288,883

(22) Filed: Nov. 3, 2011

(65) Prior Publication Data

US 2012/0116421 A1  May 10, 2012

(30) Foreign Application Priority Data

Nov. 4, 2010 (KR) .......................... 10-2010-0109201

(51) Int. Cl.
*A61B 17/12* (2006.01)
(52) U.S. Cl.
USPC .......................................... 606/144; 600/104

(58) Field of Classification Search
USPC ................. 606/144, 145, 147, 151, 205, 206; 600/104, 141
See application file for complete search history.

(56) References Cited

U.S. PATENT DOCUMENTS

| 5,690,652 | A |   | 11/1997 | Wurster et al. |
| 5,797,927 | A | * | 8/1998  | Yoon ............................ 606/144 |
| 5,843,100 | A |   | 12/1998 | Meade |

FOREIGN PATENT DOCUMENTS

| JP | 9-238947    | 9/1997 |
| WO | WO-98-27860 | 7/1998 |

* cited by examiner

*Primary Examiner* — Victor Nguyen

(57) ABSTRACT

Provided is a suturing device for organ which sutures an internal organ in front and rear directions to do a suturing operation once by clenching and unclenching a hand of an operator so that the operator easily sutures the internal organ without requiring advanced training in surgical techniques and simply and conveniently sutures the internal organ only using one hand.

20 Claims, 7 Drawing Sheets

SUTURING DEVICE FOR ORGAN

CROSS-REFERENCE TO RELATED APPLICATION

This application claims priority to and the benefit of Korean Patent Application No. 10-2010-0109201 filed on Nov. 4, 2010, which is herein incorporated by reference in its entirety.

BACKGROUND OF THE INVENTION

1. Field of the Invention

The present invention relates generally to a suturing device for organ. More particularly, the present invention relates to a suturing device for organ which sutures an internal organ in front and rear directions. Further, the suturing device of the present invention does a suturing operation once by clenching and unclenching a hand of an operator. Accordingly, the operator easily sutures the internal organ without requiring advanced training in surgical techniques and sutures the internal organ only using one hand in a simple and convenient manner.

2. Description of the Related Art

An endoscope is a piece of medical equipment designed to inspect internal organs by inserting a device into the internal organs in which lesion thereof is not known without performing an operation or autopsy. The endoscope may be classified into a bronchoscope, an esophagoscope, a gastroscope, a duodenoscope, a rectoscope, a proctoscope, and a laparoscope. In addition, other special endoscopes may include a thoracoscope, a mediastinoscope, and a cardioscope. Also, the endoscope may be classified into an endoscope manufactured as one tube that is called a laryngoscope to directly see internal organs through a naked eye, an endoscope using a lens system, an endoscope in which a camera such as a stomach camera is directly inserted into internal organs, and a fiberscope using a glass fiber.

An internal organ surgery using the laparoscope, that is a kind of endoscope, is the latest operation method in which an abdomen is incised in a size of about 0.5 cm to bore about three to four holes. Then, the laparoscope is inserted into the inside of the abdominal cavity to treat lesion using a surgical instrument while inspecting the lesion, unlike existing open surgery. The laparoscope surgery may be applied to cholecystectomy, hepatic duct stone removal, hepatolithectomy, appendectomy, or tumorectomy. When compared to the existing open surgery, in the laparoscope surgery, the pain is almost non-existent, occurrence of complications such as enteroplegia is low, the hospitalization and recovery periods are relatively short, requiring about 3 days to about 4 days when compared to a normal surgery, and a small scar is generated after the operation. Thus, the laparoscope surgery is being widely performed in recent years.

A suturing device for suturing surgical sites is used in a process for operating internal organs using the laparoscope. Technologies with respect to the suturing device are disclosed in Korean Utility Model Registration No. 20-0228438 (Publication Data: Jun. 15, 2001), titled as "SUTURE INSTRUMENT FOR CELOSCOPE SURERY" and Korean Patent Publication No. 10-2005-0033979 (Publication Data: Apr. 14, 2005), titled as "APPARATUS FOR STITCHING INTERNAL OGAN".

However, the suturing devices for organ according to the related art references, which are disclosed in Korean Utility Model Registration No. 20-0228438 and Korean Patent Publication No. 10-2005-0033979, have a limitation that the internal organs are sutured in left and right directions, but are not sutured in front and rear directions.

SUMMARY OF THE INVENTION

An aspect of the present invention provides a suturing device for organ which sutures an internal organ in front and rear directions.

Another aspect of the present disclosure provides a suturing device for organ which does a suturing operation once by clenching and unclenching a hand of an operator so that the operator easily sutures the internal organ without requiring advanced training in surgical techniques.

Further another aspect of the present disclosure provides a suturing device for organ which simply and conveniently sutures an internal organ only using one hand of an operator.

According to at least one of embodiments, a suturing device for organ includes: a main body to be grasped by a user; a needle guide handle disposed on the main body; a needle trigger handle disposed on the main body; a first arm connected to the needle guide handle; a second arm connected to the needle trigger handle; first and second rack pinions connected to the first and second arms, respectively; a rotating needle guide coaxially connected to a pinion of the first rack pinion to rotate; a needle trigger coaxially connected to a pinion of the second rack pinion to rotate; a fixed needle guide fixedly connected to the main body; and a needle fixing spring disposed on the fixed needle guide.

An arm support surrounding the first and second arms may be disposed on the main body to extend in a front direction, and a case may be disposed on an end of the arm support.

The needle guide handle may have a circular ring so that a thumb is inserted.

The main body, the needle guide handle, and the needle trigger handle may form a pistol shape, the needle guide handle may be disposed on a rear portion of the main body, and the needle trigger handle may be disposed on a middle lower portion of the main body.

A needle guide groove for guiding a needle may be defined in the rotating needle guide, and a hook for supporting the needle trigger may be disposed on the rotating needle guide.

A protrusion for fixing an organ may be disposed on the rotating needle guide.

A needle receiving groove for mounting a needle may be defined in the needle trigger.

A protrusion for fixing an organ may be disposed on the fixed needle guide.

The needle fixing spring may have a leaf spring shape.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
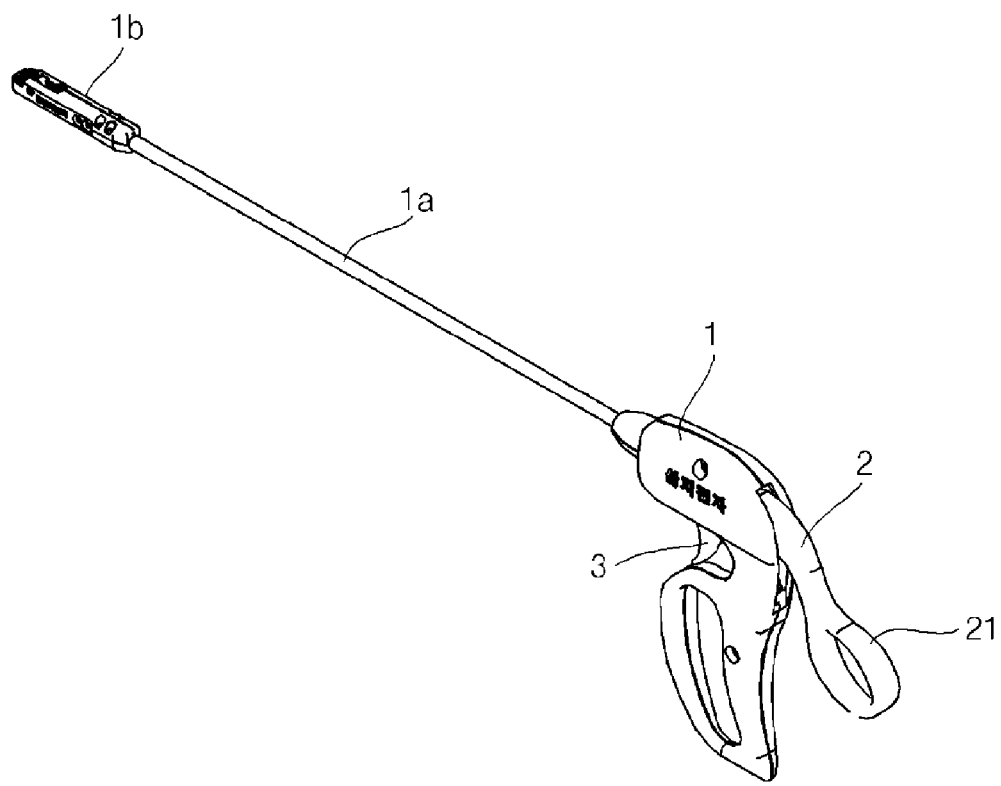
FIG. 1 illustrates a perspective view of a suturing device for organ according to an embodiment.
Figure 2:
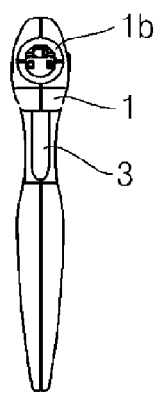
FIG. 2 illustrates a front view of a suturing device for organ according to an embodiment.
Figure 3:
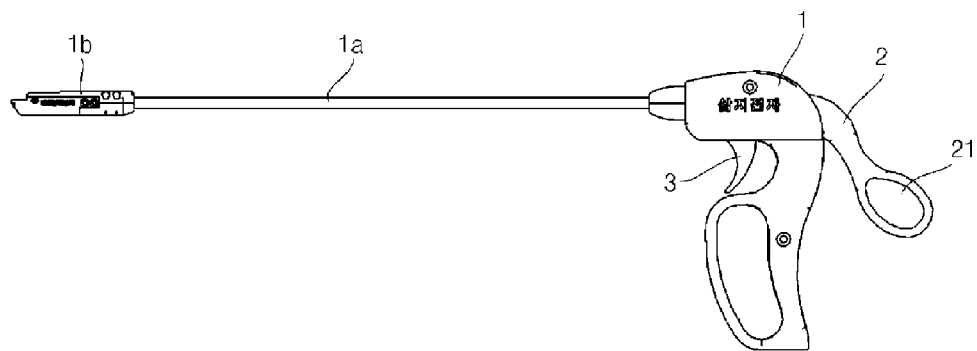
FIG. 3 illustrates a side view of a suturing device for organ according to an embodiment.
Figure 4:
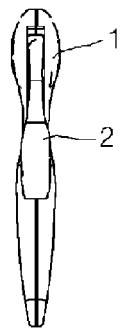
FIG. 4 illustrates a rear view of a suturing device for organ according to an embodiment.
Figure 5:
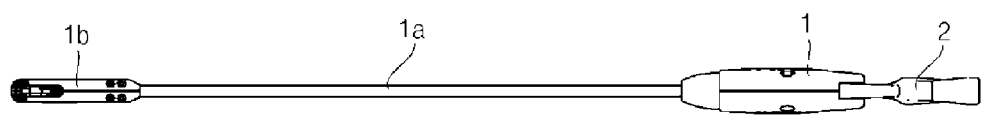
FIG. 5 illustrates a plan view of a suturing device for organ according to an embodiment.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present disclosure will be described in detail with reference to the accompanying drawings in such a manner that the technical idea of the present disclosure may easily be carried out by a person with ordinary skill in the art to which the invention pertains. Objects, operations, effects, other objects, characteristics and advantages of the present disclosure will be easily understood from an explanation of a preferred embodiment that will be described in detail below by reference to the attached drawings.

Although embodiments have been described with reference to illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims.

Referring to FIGS. 1 through 15, a suturing device for organ according to an embodiment includes a main body 1 to be grasped by a user, a needle guide handle 2 disposed on the main body 1, a needle trigger handle 3 disposed on the main body 1, a first arm 4a connected to the needle guide handle 2, a second arm 4b connected to the needle trigger handle 3, first and second rack 5a and 5b respectively connected to the first and second arms 4a and 4b, first and second pinions 6a and 6b respectively coupled to the first and second racks 5a and 5b, a rotating needle guide 7 coaxially connected to the first pinion 6a to rotate, a needle trigger 8 coaxially connected to the second pinion 6b to rotate, a fixed needle guide 9 fixedly connected to the main body 1, and a needle fixing spring 10 disposed on the fixed needle guide 9.

The main body 1, the needle guide handle 2, and the needle trigger handle 3 form a pistol shape. The needle guide handle 2 is disposed on a rear portion of the main body 1, and the needle trigger handle 3 is disposed on a middle lower portion of the main body 1.

Figure 6:
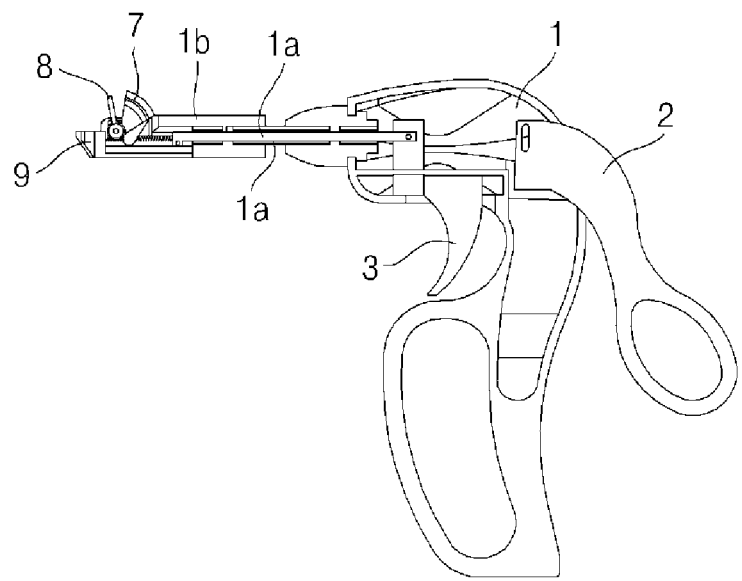
FIG. 6 illustrates a sectional view of a suturing device for organ according to an embodiment.
Figure 7:
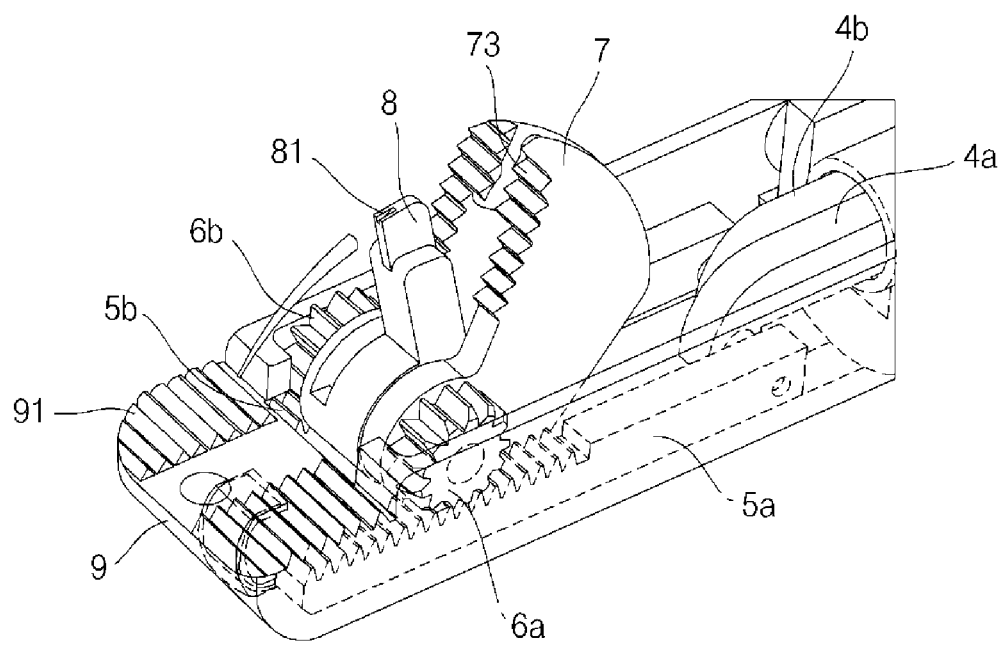
FIG. 7 illustrates a perspective view of a main part of a suturing device for organ according to an embodiment.

An arm support 1a surrounds the first and second arms 4a and 4b. The arm support 1a extends forward from the main body 1. A case 1b is disposed on an end of the arm support 1a. A length of the arm support 1a may be randomly set. FIG. 6 illustrates an arm support 1a having a length less than that of the arm support 1a of FIG. 1.

The needle guide handle 2 may have a structure in which a circular ring 21 is defined so that a thumb is inserted.

A needle guide groove 71 for guiding a needle 11 is formed in the rotating needle guide 7. Also, a hook 72 for supporting the needle trigger 8 is disposed on the rotating needle guide 7. Further, a protrusion 73 for fixing the organ is formed on the rotating needle guide 7.

A needle receiving groove 81 for mounting the needle 11 is formed in the needle trigger 8.

A protrusion 91 is formed on the fixed needle guide 9. When the protrusion 91 formed on the fixed needle guide 9 is engaged with the protrusion 73 formed on the rotating needle guide 7, the organ is fixed between the engaged protrusions 73 and 91.

The needle fixing spring 10 has a leaf spring shape.

An operation of the suturing device for organ according to an embodiment will be described below.

Figure 8:
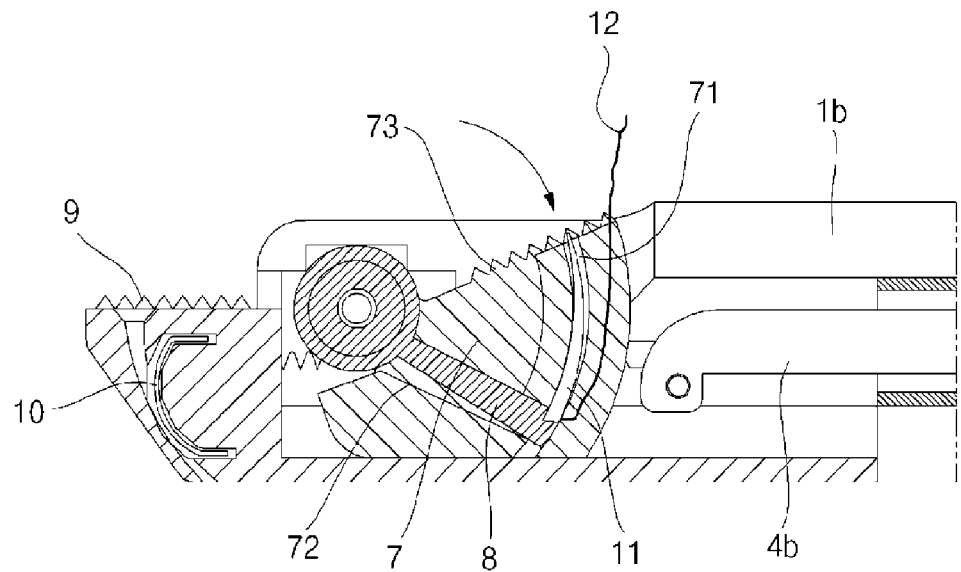
FIG. 8 illustrates a sectional view of a main part in a state in which a needle of a suturing device for organ is loaded according to an embodiment.

First, a thread 12 is threaded into the needle 11, and then the needle 11 is mounted on the needle receiving groove 81 of the needle trigger 8 through the needle guide groove 71 of the rotating needle guide 7. FIG. 8 illustrates a state in which the needle 11 is loaded on the needle receiving groove 81 of the needle trigger 8.

Figure 9:
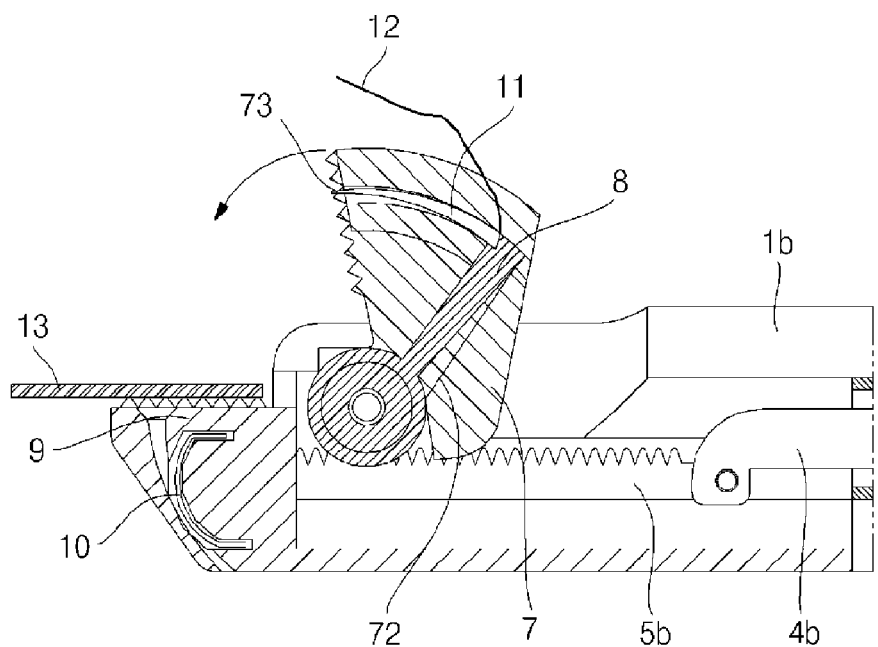
FIG. 9 illustrates a sectional view of a main part in a state where a needle guide handle of a suturing device for organ is pulled according to an embodiment.

Then, a front end of the suturing device approaches an organ 13 to be sutured to position the organ 13 on the fixed needle guide 9 as shown in FIG. 9.

Figure 10:
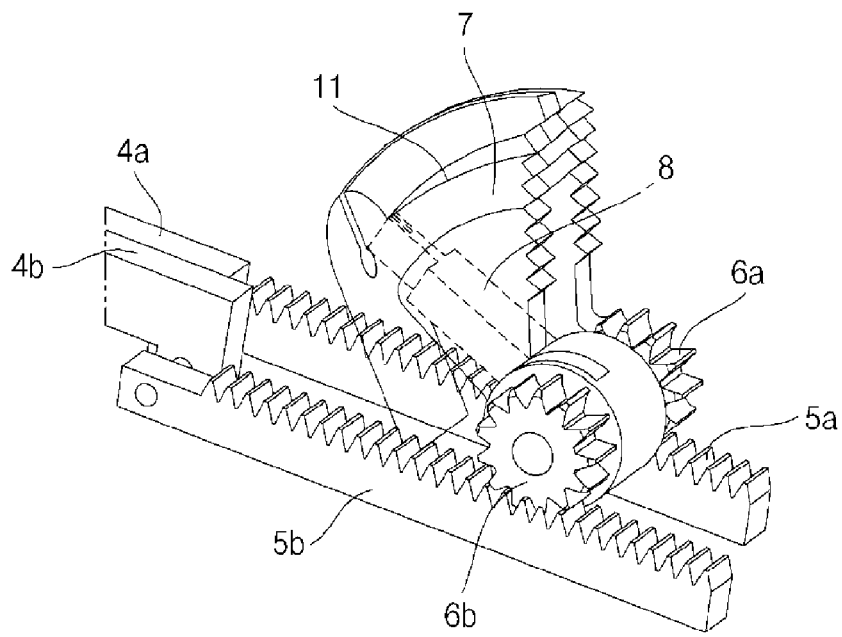
FIG. 10 illustrates a perspective view of a main part in a state where a needle guide handle of a suturing device for organ is pulled according to an embodiment.

In a state where the organ 13 is disposed on the fixed needle guide 9, when the needle guide handle 2 is pulled, the first arm 4a connected to the needle guide handle 2 is moved in a rear direction. Thus, the first rack 5a connected to the first arm 4a and the first pinion 6a converts a linear motion into a rotational motion to rotate the rotating needle guide 7 in a front direction. Here, the needle trigger 8 mounted on the hook 72 of the rotating needle guide 7 is rotated together with the rotating needle guide 7. Thus, the needle 11 mounted on the needle receiving groove 81 of the needle trigger 8 is rotated also together with the needle trigger 8. FIGS. 9 and 10 illustrate a state in which the rotating needle guide 7 and the needle trigger 8 are rotated in a front direction in a state where the needle 11 is mounted when the needle guide handle 2 is pulled.

Figure 11:
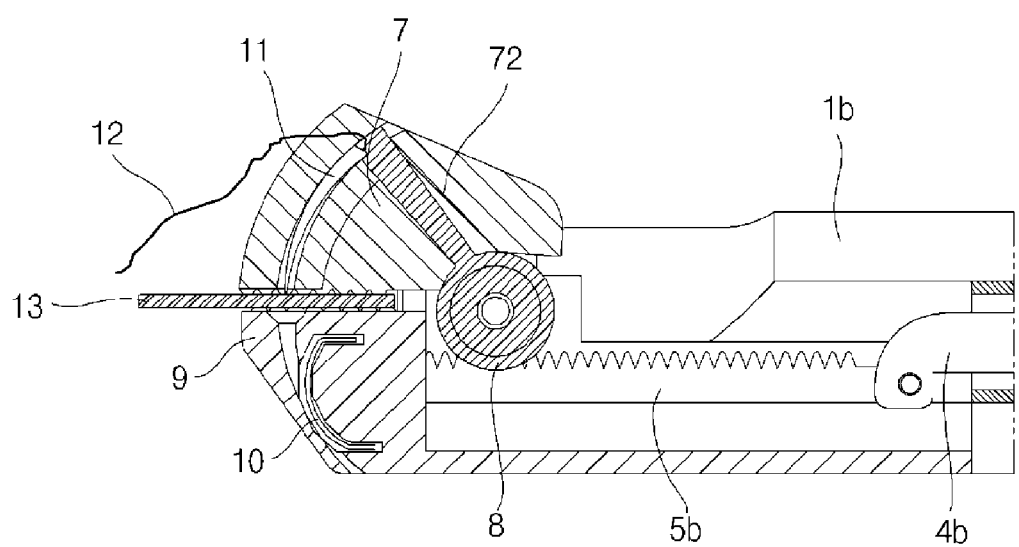
FIG. 11 illustrates a sectional view of a main part in a state in which a suturing device for organ is fixed to an internal organ according to an embodiment.

When the rotating needle guide 7 is rotated, the protrusion 73 formed on the rotating needle guide 7 contacts the organ 13 disposed on the fixed needle guide 9. In this operation, the protrusion 73 formed on the rotating needle guide 7 and the protrusion 91 formed on the fixed needle guide 9 are engaged and firmly fix the organ 13. FIG. 11 illustrates a state in which the organ 13 is fixed by the protrusion 73 of the rotating needle guide 7 and the protrusion 91 of the fixed needle guide 9.

Figure 12:
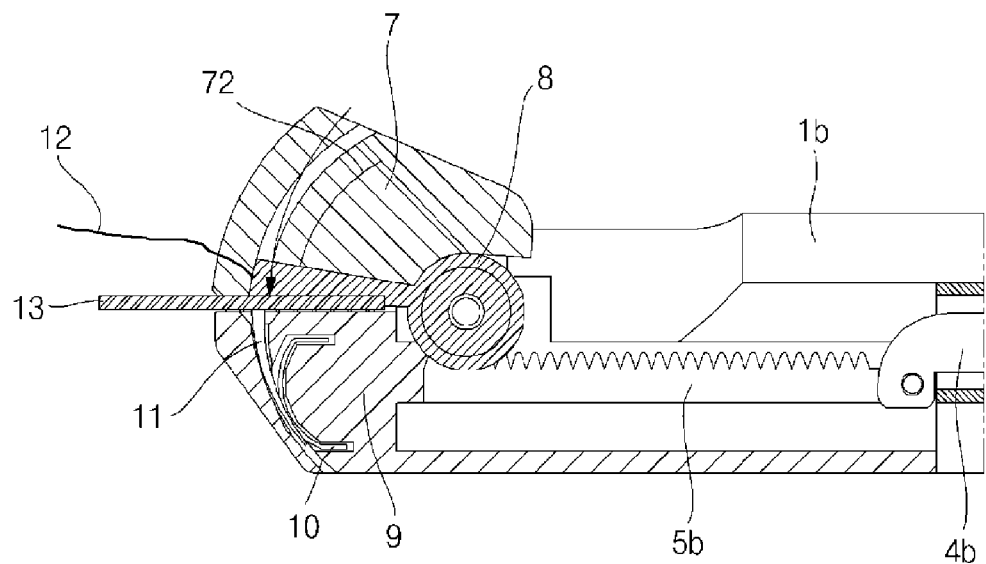
FIG. 12 illustrates a sectional view of a main part in a state where a needle trigger handle of a suturing device for organ is pulled according to an embodiment.
Figure 13:
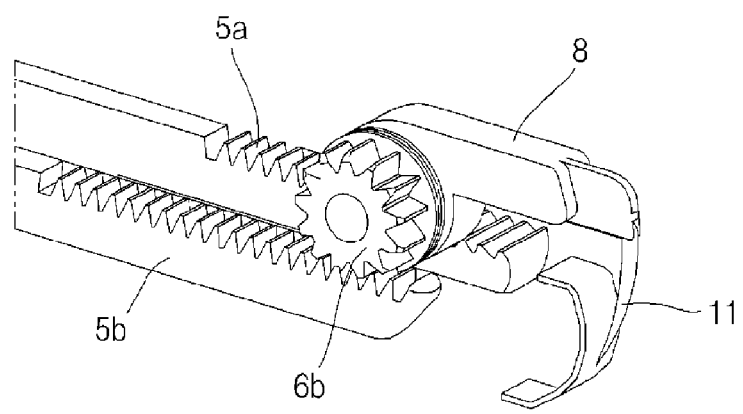
FIG. 13 illustrates a perspective view of a main part in a state where a needle trigger handle of a suturing device for organ is pulled according to an embodiment.

As described above, in the state where the organ 13 is fixed by the rotating needle guide 7 and the fixed needle guide 9, when the user pulls the needle trigger handle 3 using an index finger as if the user fires a pistol, the second arm 4b connected to the needle trigger handle 3 is slightly more moved in the rear direction. Accordingly, the second rack 5b connected to the second arm 4b and the second pinion 6b converts a linear motion into a rotational motion to slightly more rotate the needle trigger 8 in the front direction. In this operation, the needle trigger and the fixed needle guide are engaged. Here, the needle 11 mounted on the needle receiving groove 81 of the needle trigger 8 passes through the organ 13 to suture the organ 13 accordingly. The needle 11 passing through the organ 13 is maintained in a fixed state by elasticity of the needle fixing spring 10 disposed on the fixed needle guide 9. FIGS. 12 and 13 illustrate a state in which the needle 11 passes through the organ 13 and then is fixed when the needle trigger handle 3 is pulled.

Figure 14:
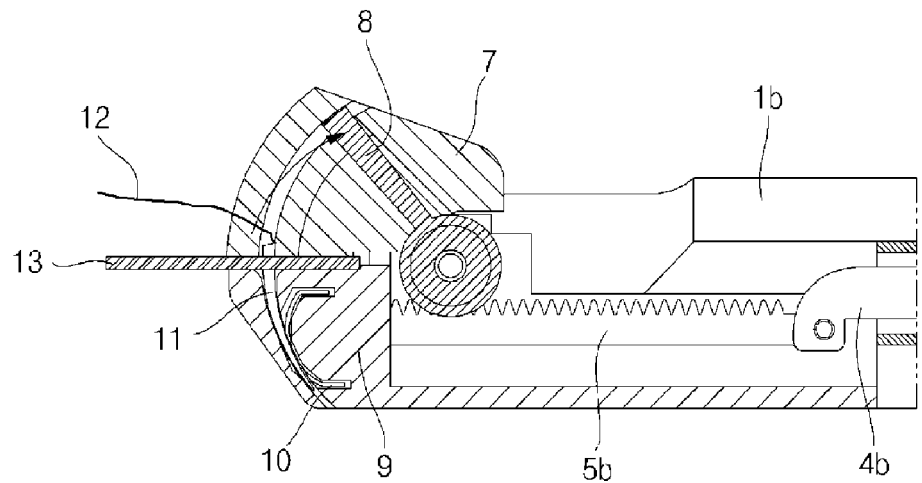
FIG. 14 illustrates a sectional view of a main part in a state where a needle trigger handle of a suturing device for organ is released according to an embodiment.

When the needle trigger handle 3 is released in the state where the needle 11 passes through the organ 13 and is fixed by the needle fixing sparing 10, the second arm 4b connected to the needle trigger handle 3 is moved in a front direction by the same distance as that of the backward movement. Thus, the second rack 5b connected to the second arm 4b and the second pinion 6b converts a linear motion into a rotational motion to rotate the needle trigger 8 in a rear direction, thereby return to the hook 72 of the rotating needle guide 7. Accordingly, the needle trigger 8 does not push the needle 11 any further. FIG. 14 illustrates a state in which the needle trigger 8 does not push the needle 11 any further to return to the hook 72 of the rotating needle guide 7 when the needle trigger handle 3 is released.

Figure 15:
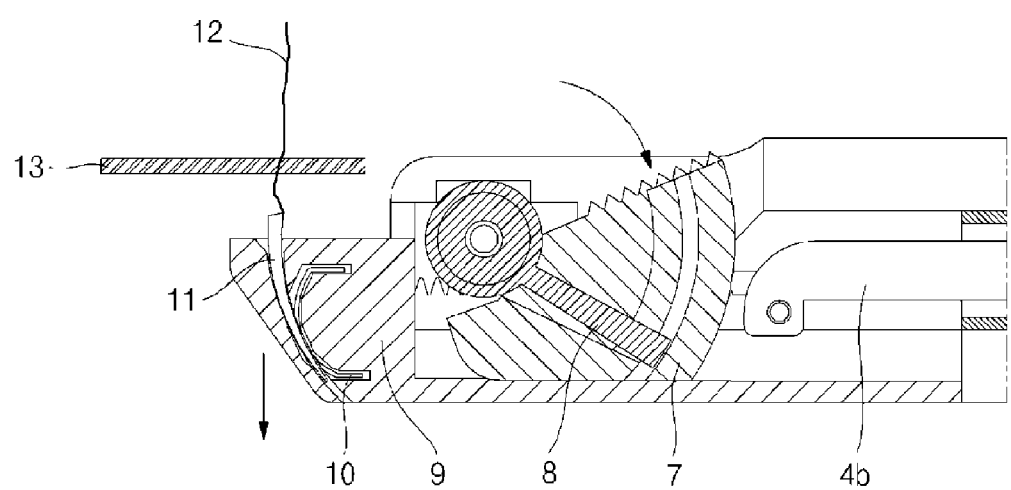
FIG. 15 illustrates a sectional view of a main part in a state where a suturing device for organ sutures an internal organ once to complete the suturing operation according to an embodiment.

As above described, when the needle guide handle 2 is released while pulling the suturing device downward in a state where the rotating needle guide 7 returns to the hook 72 of the rotating needle guide 7, the needle 11 fixed to the fixed needle guide 9 gets out from the organ 13 along the suturing device by the elasticity of the needle fixing spring 10, thereby completing the suturing operation once. At the same time, the rotating needle guide 7 and the needle trigger 8 return to their original positions. FIG. 15 illustrates a state in which the suturing operation is performed once and the rotating needle guide 7 and the needle trigger 8 return to their original positions simultaneously.

According to the embodiment, the suturing device for organ may suture the organ in the front and rear directions to do the suturing operation once by clenching and unclenching the operator's hand so that the operator easily sutures the organ without requiring advanced training in surgical techniques and simply and conveniently sutures the organ only using one hand.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A suturing device for organ comprising:
   a main body to be grasped by a user;
   a needle guide handle disposed on the main body;
   a needle trigger handle disposed on the main body;
   a first arm connected to the needle guide handle;
   a second arm connected to the needle trigger handle;
   a first rack connected to the first arm:
   a second rack connected to the second arm:
   a first pinion connected to the first rack;
   a second pinion connected to the second rack;
   a rotating needle guide coaxially connected to the first pinion to rotate;
   a needle trigger coaxially connected to the second pinion to rotate independently to the rotating needle guide;
   a fixed needle guide fixedly connected to the main body; and
   a needle fixing spring disposed on the fixed needle guide.

2. The suturing device of claim 1, further comprising an arm support disposed on the main body to extend in a front direction, and a case disposed on an end of the arm support, wherein the arm support surrounds the first arm and the second arm.

3. The suturing device of claim 2, further comprising a needle guide groove formed in the rotating needle guide for guiding a needle, and a hook formed on the rotating needle guide for supporting the needle trigger.

4. The suturing device of claim 2, further comprising a needle receiving groove formed in the needle trigger for mounting a needle.

5. The suturing device of claim 2, further comprising a protrusion disposed on the fixed needle guide for fixing an organ.

6. The suturing device of claim 2, wherein the needle fixing spring has a leaf spring shape.

7. The suturing device of claim 2, further comprising a protrusion formed on the rotating needle guide for fixing an organ.

8. The suturing device of claim 7, further comprising a protrusion disposed on the fixed needle guide for fixing an organ.

9. The suturing device of claim 8, wherein the protrusion disposed on the fixed needle guide and the protrusion disposed on the fixed needle guide are engaged when the rotating needle guide and the needle trigger are rotated in a front direction by pulling the needle guide handle in a rear direction.

10. The suturing device of claim 9, wherein the needle trigger and the fixed needle guide are engaged when the needle trigger is rotated in a front direction by pulling the needle guide handle and the needle trigger handle in a rear direction.

11. The suturing device of claim 1, wherein the needle guide handle has a circular ring so that a thumb is inserted.

12. The suturing device of claim 1, wherein the main body, the needle guide handle, and the needle trigger handle form a pistol shape, the needle guide handle is disposed on a rear portion of the main body, and the needle trigger handle is disposed on a middle lower portion of the main body.

13. The suturing device of claim 1, further comprising a needle guide groove formed in the rotating needle guide for guiding a needle, and a hook formed on the rotating needle guide for supporting the needle trigger.

14. The suturing device of claim 1, further comprising a protrusion formed on the rotating needle guide for fixing an organ.

15. The suturing device of claim 14, further comprising a protrusion disposed on the fixed needle guide for fixing an organ.

16. The suturing device of claim 15, wherein the protrusion disposed on the fixed needle guide and the protrusion disposed on the fixed needle guide are engaged when the rotating needle guide and the needle trigger are rotated in a front direction by pulling the needle guide handle in a rear direction.

17. The suturing device of claim 16, wherein the needle trigger and the fixed needle guide are engaged when the needle trigger is rotated in a front direction by pulling the needle guide handle and the needle trigger handle in a rear direction.

18. The suturing device of claim 1, further comprising a needle receiving groove formed in the needle trigger for mounting a needle.

19. The suturing device of claim 1, further comprising a protrusion disposed on the fixed needle guide for fixing an organ.

20. The suturing device of claim 1, wherein the needle fixing spring has a leaf spring shape.

* * * * *